(12) United States Patent
Andrienko

(10) Patent No.: US 8,266,742 B2
(45) Date of Patent: Sep. 18, 2012

(54) BIOMETRIC BED CONFIGURATION

(75) Inventor: Kirill Andrienko, Harrison, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 128 days.

(21) Appl. No.: 12/961,064

(22) Filed: Dec. 6, 2010

(65) Prior Publication Data

US 2012/0137436 A1 Jun. 7, 2012

(51) Int. Cl.
*A61G 7/018* (2006.01)
*G08B 1/08* (2006.01)

(52) U.S. Cl. ......... 5/600; 5/424; 340/573.1; 340/286.07

(58) Field of Classification Search .............. 5/600, 611, 5/613, 616–618, 424; 340/573.1, 286.07
See application file for complete search history.

(56) References Cited

U.S. PATENT DOCUMENTS

| | | |
|---|---|---|
| 4,044,286 A | 8/1977 | Adams et al. |
| 4,506,569 A | 3/1985 | Brown et al. |
| 4,539,560 A | 9/1985 | Fleck et al. |
| 4,934,468 A | 6/1990 | Koerber, Sr. et al. |
| 5,161,274 A | 11/1992 | Hayes et al. |
| 5,561,412 A | 10/1996 | Novak et al. |
| 5,636,394 A | 6/1997 | Bartley |
| 5,699,038 A | 12/1997 | Ulrich et al. |
| 5,715,548 A | 2/1998 | Weismiller et al. |
| 5,771,511 A | 6/1998 | Kummer et al. |
| 5,838,223 A | 11/1998 | Gallant et al. |
| 6,021,533 A | 2/2000 | Ellis et al. |
| 6,067,019 A | 5/2000 | Scott |
| 6,133,837 A | 10/2000 | Riley |
| 6,185,767 B1 | 2/2001 | Brooke et al. |
| 6,208,250 B1 | 3/2001 | Dixon et al. |
| 6,279,183 B1 | 8/2001 | Kummer et al. |
| 6,320,510 B2 | 11/2001 | Menkedick et al. |
| 6,321,878 B1 | 11/2001 | Mobley et al. |
| 6,336,235 B1 | 1/2002 | Ruehl |
| 6,362,725 B1 | 3/2002 | Ulrich et al. |
| 6,505,368 B1 | 1/2003 | Ellis et al. |
| 6,584,628 B1 | 7/2003 | Kummer et al. |
| 6,691,346 B2 | 2/2004 | Osborne et al. |
| 6,694,549 B2 | 2/2004 | Perez et al. |
| 6,708,358 B2 | 3/2004 | Hensley |
| 6,791,460 B2 | 9/2004 | Dixon et al. |
| 6,876,303 B2 | 4/2005 | Reeder et al. |
| 6,892,405 B1 | 5/2005 | Dimitriu et al. |
| 6,957,461 B2 | 10/2005 | Osborne et al. |
| 6,978,500 B2 | 12/2005 | Osborne et al. |
| 7,092,376 B2 | 8/2006 | Schuman |
| 7,171,708 B2 | 2/2007 | Osborne et al. |
| 7,237,287 B2 | 7/2007 | Weismiller et al. |
| 7,260,860 B2 | 8/2007 | Chambers et al. |
| 7,296,312 B2 | 11/2007 | Menkedick et al. |
| 7,315,535 B2 | 1/2008 | Schuman |
| 7,319,386 B2 | 1/2008 | Collins, Jr. et al. |
| 7,325,265 B2 | 2/2008 | Hornbach et al. |
| 7,330,127 B2 | 2/2008 | Price et al. |

(Continued)

*Primary Examiner* — Robert G Santos
(74) *Attorney, Agent, or Firm* — Barnes & Thornburg LLP

(57) ABSTRACT

A bed has one or more electronically-controllable features. Input-output devices are used by persons to control the electronically-controllable features. A biometric input-output device obtains biometric data from persons who desire to control one or more of the electronically-controllable features. The bed may restrict access to or modify one or more of the electronically-controllable features based on the biometric data.

20 Claims, 4 Drawing Sheets

U.S. PATENT DOCUMENTS

| | | | |
|---|---|---|---|
| 7,389,552 B1 * | 6/2008 | Reed et al. | 5/86.1 |
| 7,406,731 B2 | 8/2008 | Menkedick et al. | |
| 7,443,302 B2 | 10/2008 | Reeder et al. | |
| 7,451,506 B2 | 11/2008 | Kummer et al. | |
| 7,454,805 B2 | 11/2008 | Osborne et al. | |
| 7,458,119 B2 | 12/2008 | Hornbach et al. | |
| 7,464,605 B2 | 12/2008 | Douglas et al. | |
| 7,469,436 B2 | 12/2008 | Meyer et al. | |
| 7,480,951 B2 | 1/2009 | Weismiller et al. | |
| 7,487,562 B2 | 2/2009 | Frondorf et al. | |
| 7,500,280 B2 | 3/2009 | Dixon et al. | |
| 7,520,006 B2 | 4/2009 | Menkedick et al. | |
| 7,523,515 B2 | 4/2009 | Allen et al. | |
| 7,533,429 B2 | 5/2009 | Menkedick et al. | |
| 7,610,637 B2 | 11/2009 | Menkedick et al. | |
| 7,610,638 B2 | 11/2009 | Kramer et al. | |
| 7,617,555 B2 | 11/2009 | Romano et al. | |
| 7,657,956 B2 | 2/2010 | Stacy et al. | |
| 7,676,862 B2 | 3/2010 | Poulos et al. | |
| 7,676,872 B2 * | 3/2010 | Block et al. | 5/690 |
| 7,690,059 B2 | 4/2010 | Lemire et al. | |
| 7,715,387 B2 | 5/2010 | Schuman | |
| 7,743,441 B2 | 6/2010 | Poulos et al. | |
| 7,757,318 B2 | 7/2010 | Poulos et al. | |
| 7,779,493 B2 * | 8/2010 | Lemire et al. | 5/600 |
| 7,779,494 B2 | 8/2010 | Poulos et al. | |
| 7,784,128 B2 | 8/2010 | Kramer | |
| 8,051,513 B2 * | 11/2011 | Reed et al. | 5/627 |
| 8,155,918 B2 * | 4/2012 | Reed et al. | 702/150 |
| 8,156,586 B2 * | 4/2012 | Reed et al. | 5/611 |
| 2004/0231052 A1 | 11/2004 | Gladney | |
| 2005/0203493 A1 | 9/2005 | Kuroda et al. | |
| 2006/0107459 A1 | 5/2006 | Gladney | |
| 2007/0130692 A1 | 6/2007 | Lemire et al. | |
| 2007/0132597 A1 | 6/2007 | Rodgers | |
| 2007/0136102 A1 | 6/2007 | Rodgers | |
| 2007/0180616 A1 | 8/2007 | Newkirk et al. | |
| 2007/0210917 A1 | 9/2007 | Collins, Jr. et al. | |
| 2008/0015903 A1 | 1/2008 | Rodgers | |
| 2008/0021731 A1 | 1/2008 | Rodgers | |
| 2008/0201429 A1 | 8/2008 | Barbell et al. | |
| 2008/0224861 A1 | 9/2008 | McNeely et al. | |
| 2008/0235872 A1 | 10/2008 | Newkirk et al. | |
| 2009/0091458 A1 | 4/2009 | Deutsch | |
| 2009/0165207 A1 * | 7/2009 | Reed et al. | 5/611 |
| 2009/0165208 A1 * | 7/2009 | Reed et al. | 5/611 |
| 2009/0222988 A1 * | 9/2009 | Reed et al. | 5/627 |
| 2009/0310741 A1 | 12/2009 | Borghese et al. | |
| 2010/0088119 A1 | 4/2010 | Tipirneni | |

* cited by examiner

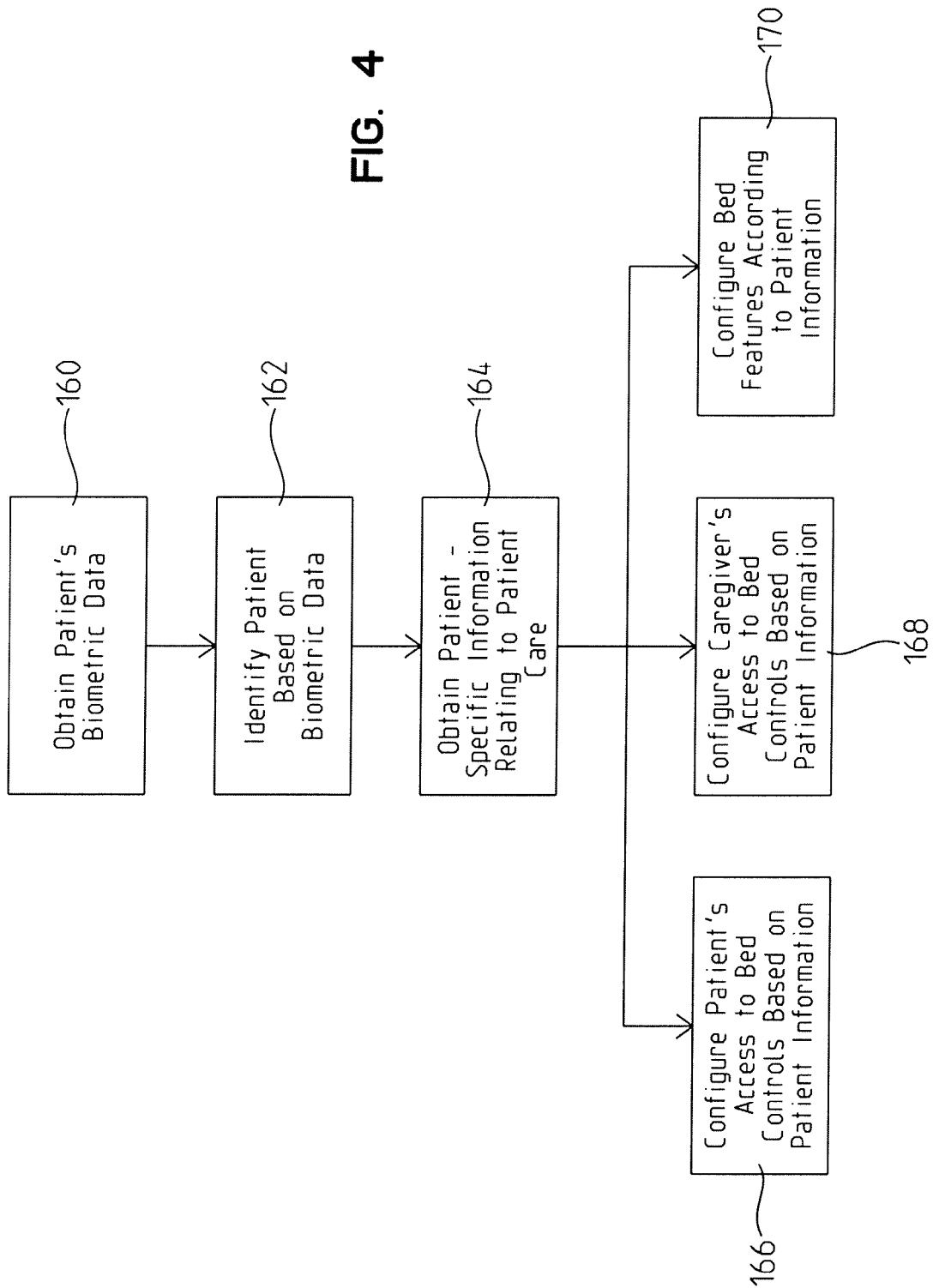

BIOMETRIC BED CONFIGURATION

BACKGROUND

This disclosure relates generally to beds. More particularly, this disclosure relates to beds that have one or more electronically-controllable features, such as raising or lowering different sections of the bed, weighing a person positioned on the bed, monitoring the bed to detect a person exiting the bed, communicating with a healthcare communication system (such as a nurse call system), or providing a mattress therapy such as pressure relief, percussion, vibration, or rotation. Such beds may be found, for example, in healthcare facilities, homes, and other locations in which care is provided. Some examples of such beds are the TotalCare® Bed System, the VersaCare® bed, the CareAssist® bed, and the ExcelCare® bed, which are available from the Hill-Rom Company, Inc. Some examples of beds that have electronically-controllable features are disclosed in U.S. Pat. Nos. 6,957,461 and 6,279,183.

Sometimes, beds that have electronically-controllable functions are equipped with an internal bed communication network. For example, one or more bed controllers and bed function modules may be connected to the bed network, so that control signals from the bed controller(s) are communicated to the appropriate bed function modules via the bed network. Some examples of beds that have an internal bed network are described in U.S. Pat. Nos. 5,771,511; 6,584,628; 7,237,287; 7,296,312; 7,451,506; 7,480,951; and 7,657,956.

Beds that have electronically-controllable functions may have one or more user control modules, which allow a patient, caregiver or other person to control certain features of the bed. Typically, user control modules are mounted to a siderail, endboard, or other support structure of the bed. Some examples of user control modules are disclosed in U.S. Pat. Nos. 6,320,510 and 7,296,312; as well as U.S. Patent Application Publication Nos. 2007/0180616 and 2008/0235872.

Some user control modules limit access to certain bed features. Some examples of user interfaces that have lockout/enable buttons are disclosed in U.S. Patent Nos. 6,320,510 and 7,296,312. An example of a system in which patient controls are enabled or disabled in response to the presence or absence of a caregiver is disclosed in U.S. Pat. Nos. 6,876,303 and 7,443,302.

Some beds can be connected to a healthcare facility's computer system and/or other external computer systems, to send data generated at the bed to the external system. For example, a bed may have sensors that detect when a patient has exited a bed, if the bed's brake is not set, or when a siderail is down. Upon detecting such a condition, the bed may send an alert signal to a master station of the healthcare facility's nurse call system. The master station may then send an electronic notification to a remote device, such as a patient station or a mobile unit used by a caregiver. Some examples of systems in which beds may communicate data to a hospital communication system are disclosed in U.S. Pat. Nos. 7,319,386; 6,362,725; and 5,699,038; and U.S. Patent Application Publication Nos. 2008/0224861 and 2007/0210917.

SUMMARY

The present invention comprises one or more of the features recited in the appended claims and/or the following features which, alone or in any combination, may comprise patentable subject matter.

According to one aspect of this disclosure, a bed system includes a bed having at least one electronically-controllable feature, and a biometric sensor operably coupled to the bed. The biometric sensor receives a first input from a user. The bed system also includes a non-biometric input device operably coupled to the bed, which receives a second input from the user to activate an electronically-controllable feature of the bed. The bed system also includes a controller operably coupled to the bed, the biometric sensor, and the non-biometric input device. The controller analyzes the first input and outputs a control signal to enable or disable the non-biometric input device based on the first input.

The controller may uniquely identify the user based on the first input. The controller may identify a characteristic of the user based on the first input. The controller may determine whether access to an electronically-controllable feature of the bed should be enabled or disabled based on the characteristic of the user. The controller may determine whether the user is a patient or a caregiver based on the first input.

The bed system may include a communication link operably coupled to the controller to provide data representative of the first input to a healthcare information system and to provide data relating to the user from the healthcare information system to the controller. The controller may determine whether access to an electronically-controllable feature of the bed should be modified based on the data from the healthcare information system.

According to another aspect of this disclosure, a bed system includes a bed having at least one electronically-controllable feature, and a biometric sensor operably coupled to the bed. The biometric sensor receives a first input from a user. The bed system also includes a non-biometric input device operably coupled to the bed, which receives a second input from the user and activates or deactivates an electronically-controllable feature of the bed in response to the second input. The bed system also includes a controller operably coupled to the bed, the biometric sensor, and the non-biometric input device. The controller analyzes the first input and determines based on the first input whether to activate the electronically-controllable feature of the bed in response to the second input.

The biometric sensor may be integrated with the input device. The biometric sensor may be spaced from the input device. The bed system may include a siderail coupled to the bed, where the biometric sensor is mounted to the siderail. The bed system may include an endboard coupled to the bed, where the biometric sensor is mounted to the endboard. The biometric sensor may also be coupled to a pendant controller.

The bed system may include a second biometric sensor, where the biometric sensor is mounted to the bed at a first location, the second biometric sensor is mounted to the bed at a second location spaced from the first location, the second biometric sensor is configured to receive a third input from a user, and the controller analyzes the third input to determine whether to activate an electronically-controllable feature of the bed based on the third input.

According to another aspect of this disclosure, a bed system includes a bed having at least one electronically-controllable feature, and a biometric sensor operably coupled to the bed. The biometric sensor receives a first input from a user. The bed system also includes a non-biometric input device operably coupled to the bed, which receives a second input from the user. The bed system also includes a controller operably coupled to the bed, the biometric sensor, and the non-biometric input device. The controller analyzes the first input, modifies an electronically-controllable feature of the bed in response to the first input, and initiates operation of the modified electronically-controllable feature in response to the second input.

The controller may determine whether the user is a patient or a caregiver based on the first input and may configure the electronically-controllable feature based on whether the user is a patient or a caregiver. The non-biometric input device may include a graphical user interface. The controller may determine whether the user is a patient, a caregiver, a visitor, or another person based on the first input, and the controller may configure the graphical user interface based on whether the user is a patient, a caregiver, a visitor, or another person.

The controller may determine a characteristic of the user based on the first input and may configure the electronically-controllable feature based on the characteristic of the user. The electronically-controllable feature may be a bed articulation feature, the characteristic of the user may indicate that the user has a health condition, and the controller may adjust the bed articulation feature based on the health condition.

The electronically-controllable feature may be a support surface feature, and the controller may adjust the support surface feature based on the characteristic of the user. The controller may automatically adjust one or more of a time parameter, a speed parameter, an articulation parameter, a length adjustment parameter, a width adjustment parameter, and an alarm parameter relating to the electronically-controllable feature based on the characteristic of the user.

BRIEF DESCRIPTION OF THE DRAWINGS

The detailed description particularly refers to the following figures, in which:

FIG. 4 is a flow diagram illustrating another biometric bed configuration process executable by the bed control system.

DETAILED DESCRIPTION

Figure 1:
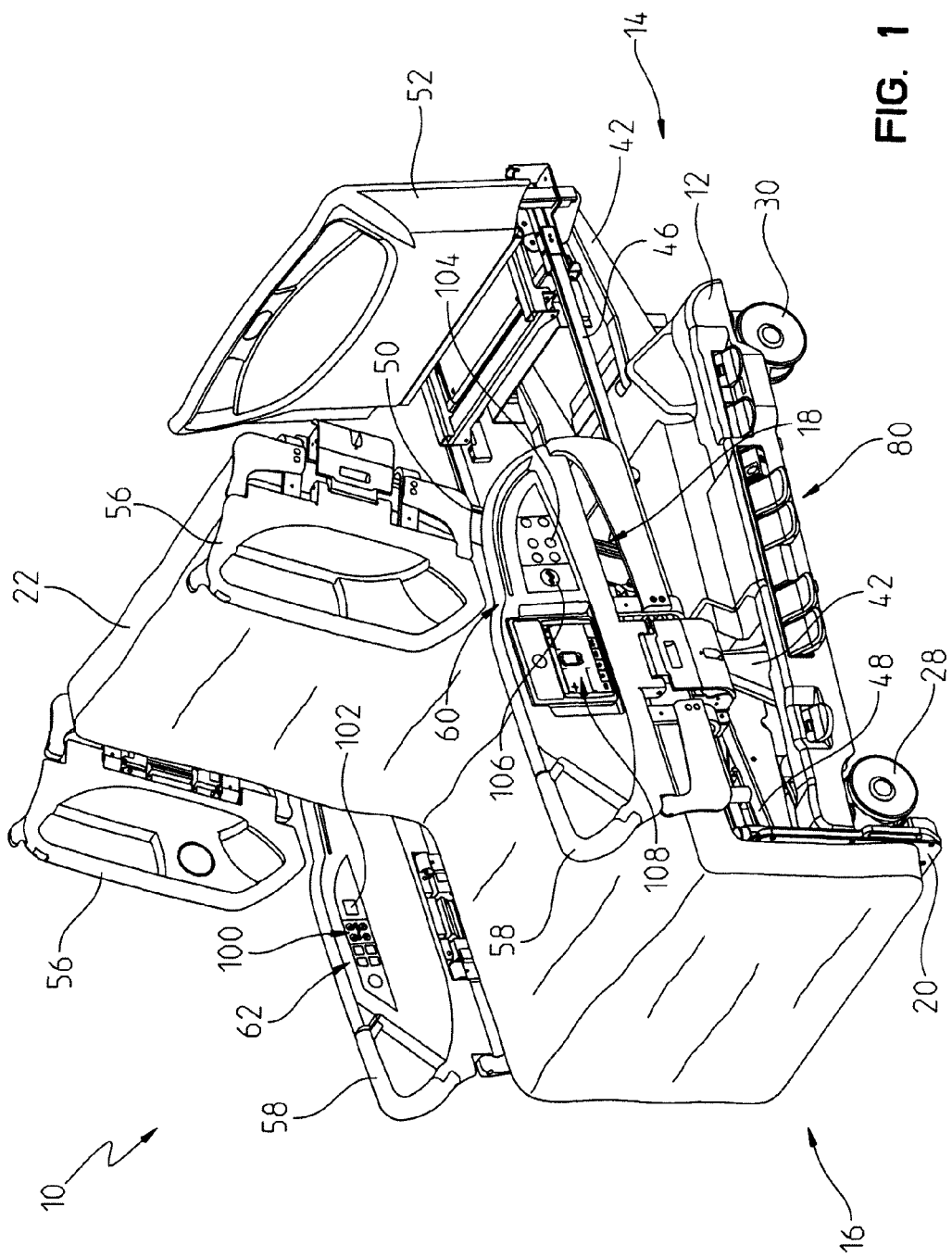
FIG. 1 is a perspective view of a bed in a chair position.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a bed 10 is shown. While the bed 10 is a type of bed typically used in hospitals and other facilities in which health care is provided, aspects of the present disclosure are applicable to any type of bed or similar structure that has electronically-controllable features, including but not limited to stretchers and other patient support structures.

The bed 10 has one or more electronically-controllable bed functions or features, which may include, but are not limited to: adjusting the position, length, or width of the bed, raising, lowering, or pivoting a section of the bed, weighing a person positioned on the bed, inflating, deflating, or adjusting inflation in one or more sections of the mattress, laterally rotating a person positioned on the bed, providing percussion, vibration, pulsation, or alternating pressure therapy to a person positioned on the bed, monitoring a person's position or orientation on or relative to the bed, generating an alert if a person on the bed changes position or exits the bed or is in a certain position for too long, weighing a person positioned on the bed, enabling a person positioned on the bed to communicate with a caregiver located outside the person's room through an electrical network or telecommunications system, and exchanging data and/or instructions with other devices, equipment, and/or computer systems. Accordingly, the bed 10 has its own supply of electrical power (e.g. a battery) and/or a connector (not shown) that connects the bed 10 to a supply of AC electrical power (e.g. a wall outlet).

While the bed 10 often assumes a flat or horizontal position, FIG. 1 shows the bed 10 in a chair position. The bed 10 may assume other positions, as described below.

The bed 10 includes a base 12, which has a head end 14 and a foot end 16 spaced from the head end 14. The base 12 is supported by a number of casters, including casters 28, 30. The casters 28, 30, each include one or more wheels that movably support the bed 10 relative to a floor or other surface, in one or more directions. The base 12 and/or one or more of the casters 28, 30 may have an electronically or mechanically-controlled brake and/or steer lock mechanism coupled thereto. A proximity sensor, binary switch, or other suitable type of sensor may be coupled to the caster brake/steer mechanism, and coupled to a bed controller 122, described below, to enable the bed controller 122 to monitor the status of the caster brake/steer mechanism. For example, the bed controller 122 may enable a caregiver to set or release a caster brake by pressing a button that is electronically connected to the bed controller 122. The bed controller 122 may issue an audible or visual signal to indicate whether a caster brake is or is not set. An example of a bed having a sensor or switch that detects the status of a brake mechanism is disclosed in U.S. Pat. No. 6,321,878.

The bed controller 122 may enable a caregiver to configure the brake/steer mechanism and/or turn braking and steering features on or off for a particular patient, or to configure braking and steering features differently for different patients, or differently for different patient conditions, or differently for different caregivers. For example, some caregivers may prefer a loud, audible notification while others may prefer a visual notification, when being alerted to a bed condition. The bed controller 122 may include computer logic to customize the alert for individual caregivers, based on the biometric data.

As another example, some healthcare facility staff or other persons (such as visitors) may not have the requisite authority to configure or operate the brake and/or steering features. Accordingly, the bed controller 122 may include computer logic to restrict or prevent operation of these features by certain persons, or to enable these features only for certain other persons, based on the biometric data of persons accessing the bed.

A frame 46 is coupled to and supported by the base 12. A lift mechanism, which includes lift arms 42, is configured to raise, lower, and tilt the frame 46 relative to the base 12. A weigh scale may be coupled to the frame 46, using existing or newly developed techniques. Some examples of beds with built-in weigh scales and associated displays and user controls are disclosed in U.S. Pat. Nos. 4,934,468; 5,715,548; 6,336,235; 7,296,312; and 7,500,280.

The built-in weigh scale may be electronically controlled. For example, the bed controller 122 may enable a caregiver to weigh a person positioned on the bed 10 by pressing a button that is electronically connected to the bed controller 122. The person's weight as determined by the on-board weigh scale may be displayed (e.g. via an LCD display) and stored in memory. If the bed is not provided with a weigh scale, the bed controller 122 may enable a caregiver to input the person's weight as determined by other means, for storage in memory and use by the bed controller 122. Alternatively or in addition, the bed controller 122 may include computer logic to obtain the person's weight information from an EMR database or other stored location, after identifying the person based on the person's biometric data obtained at the bed. The bed controller 122 may use the person's weight information to configure pressure settings for a mattress 22 used in connection with the bed 10, and/or to adjust the articulation of the bed 10.

As another example, some healthcare facility staff or other persons (such as visitors) may not have the requisite authority to configure or operate the patient weighing features of the bed 10. The bed controller 122 may include computer logic to restrict or prevent operation of these features by certain persons, or to enable these features only for certain other persons, based on the biometric data of persons accessing the bed.

A deck 18 is coupled to and supported by the frame 46. The deck 18 is configured to support the mattress 22, which, in turn, may support a person positioned thereon. The deck 18 has a number of sections including, in the illustrated embodiment, a foot section 20 and a head section 50. The deck 18 also includes a torso section 48. In the illustrated embodiment, the torso section 48 includes a separate thigh section 48 and seat section (view obstructed). In other embodiments, the torso section 48 may include a single deck section (e.g. a seat/thigh section) rather than two separate deck sections.

The foot section 20 and the head section 50 are pivotable, such that the deck 18 may assume a number of different positions as noted above. In the chair position, the foot section 20 is pivoted downwardly toward the base 12 and the head section 50 is pivoted upwardly away from the frame 46. In the illustrated embodiment, the thigh section 48 is also pivotable relative to the frame. For example, the thigh section 48 may be pivoted upwardly away from the frame 46 to support the patient's knees when the head section 50 is elevated. Other positions that the bed 10 may assume include a low position, in which the frame 46 is lowered toward the base 12, a Trendelenburg position, a Reverse Trendelenburg position, and any position between the flat position and the chair position.

While not visible in the view of FIG. 1, the bed 10 has a number of powered actuators, such as electric linear actuators or hydraulic cylinders, which enable the bed to assume different positions. One or more actuators are coupled to the frame 46 using existing or new techniques to enable raising, lowering, and tilting of the frame 46 relative to the base 12. Other actuators are coupled to each of the deck sections 20, 48, 50 to enable pivoting of the deck sections 20, 48, 50 relative to the frame 46. Examples of such actuators are disclosed in U.S. Pat. Nos. 5,715,548; 6,185,767; 6,336,235; 6,694,549; 7,454,805; 6,708,358; 7,325,265; 7,458,119; 7,523,515; 7,610,637; 7,610,638; and 7,784,128.

In general, each of the actuators is coupled to a power plant (e.g. a motor) and has an extending/retracting arm or linkage. One end of the arm or linkage is coupled to the power plant and the other end is coupled to the frame 46 or the relevant deck section 20, 48, 50. The power plant drives the arm or linkage in one direction to provide movement of the frame 46 or deck section 20, 48, 50 in one direction (e.g. raising or pivoting upwardly), and drives the arm or linkage in the opposite direction to provide movement of the frame 46 or deck section 20, 48, 50 in the other direction (e.g. lowering or pivoting downwardly). The power plant is responsive to control signals issued by the bed controller 122. When movement of a bed section is requested, the controller 122 determines the duration of the requested movement (i.e. how far the associated arm or linkage is to be extended or retracted, as the case may be) and the speed at which the requested movement is to be accomplished (i.e. how slowly or quickly the associated arm or linkage is to be extended or retracted), and sends a corresponding control signal or signals to the power plant.

The bed 10 may include one or more sensors that are coupled to the actuators to monitor the speed or progress of movement or articulation of a bed section. For example, a bed-not-down sensor may be coupled to the foot section of the deck 18 and/or to the lift mechanism 42, to alert a caregiver if the bed 10 is not in a position that is suitable for egress, or for other reasons. In response to output of a bed-not-down sensor, the bed controller 122 may issue a visual and/or audible signal and/or communication signal indicating that the bed or a section thereof is not in its low or 'down' position.

The bed controller 122 may enable a caregiver to configure the chair egress or other egress positions of the bed, and/or configure the bed-not-down sensor differently for different patients, or differently for different patient conditions, or differently for different caregivers, using the biometric data. For example, for some patients, it may not be appropriate to move the bed into an egress position without another attendant being in the room. The bed controller 122 may include computer logic to lock out one or more of the egress features of the bed 10, for certain individual patients, based on the biometric data obtained at the bed.

As another example, some caregivers may prefer a loud, audible notification while others may prefer a visual notification, when being alerted to a bed condition. The bed controller 122 may include computer logic to customize the alert for individual caregivers, based on the biometric data obtained at the bed.

As a further example, some healthcare facility staff or other persons (such as visitors) may not have the requisite authority to configure or operate the chair position features of the bed 10. The bed controller 122 may include computer logic to restrict or prevent operation of these features by certain persons, or to enable these features only for certain other persons, based on the biometric data of persons accessing the bed.

The bed 10 may be equipped with additional sensors that are configured to detect other conditions of the bed. For example, some beds have position sensors (such as force sensors) that detect force applied to the bed at different locations on the bed. The bed controller 122 includes executable instructions that determine, based on the output of the force sensor or sensors, the position of a patient relative to the bed (e.g. the patient has exited the bed, is on the edge of the bed, or is sitting up in bed). The bed controller 122 may then issue a visual and/or audible signal and/or communication signal relating to the patient's position. Some examples of beds having patient position monitoring features are disclosed in U.S. Pat. Nos. 6,067,019; 6,133,837; 6,208,250; 6,791,460; and 7,464,605.

The bed controller 122 may enable a caregiver to turn patient position monitoring features on or off for a particular patient, or to configure a patient position monitoring feature differently for different patients or differently for different patient conditions. For example, for one patient, the caregiver may configure the patient position monitoring feature to only send an alert if the patient has exited the bed, while for another patient, the caregiver may configure the patient position monitoring feature to send an alert if the patient is detected as sitting on the edge of the bed or if the patient has exited the bed.

The bed controller 122 may also enable the patient position monitoring features to be configured differently for different caregivers. For example, some caregivers may prefer a loud, audible notification while others may prefer a visual notification, while still others may prefer a silent notification (e.g. a "vibrate" setting on a mobile device) when being alerted to a patient position condition.

Also, some healthcare facility staff or other persons (such as visitors) may not have the requisite authority to configure or operate the patient position monitoring features of the bed 10. The bed controller 122 may include computer logic to restrict or prevent operation of these features by certain persons, or to enable these features only for certain other persons, based on the biometric data of persons accessing the bed.

The bed 10 may be equipped with angle or orientation sensors, such as ball switches, potentiometers, inclinometers, accelerometers, or the like, which detect changes in the orientation of the bed or one section of the bed relative to another section of the bed. For example, an orientation sensor may be used to determine the angle of the head section 50 or the foot section 20 of the bed relative to the bed frame 46 or to the horizontal. The bed controller 122 includes executable instructions that determine, based on the output of the orientation sensor or sensors, the orientation of the bed or a section thereof. The bed controller 122 may then issue a visual and/or audible signal and/or communication signal relating to the bed's orientation. For example, the bed controller 122 may alert a caregiver if the angle of the head section 50 is less than 30 degrees above horizontal. An example of a bed that has a head angle alarm feature is disclosed in U.S. Pat. No. 7,487,562.

The bed controller 122 may enable a caregiver to turn head angle monitoring features on or off for a particular patient, or to configure a head angle monitoring feature differently for different patients, or differently for different patient conditions. For example, for one patient, the caregiver may configure the head angle monitoring feature to send an alert if the head angle of the bed has been less than 30 degrees for a certain length of time, while for another patient, the caregiver may configure the head angle monitoring feature to send an alert if the head angle of the bed has been less than 30 degrees for a different length of time.

The bed controller 122 may also enable the head angle monitoring features to be configured differently for different caregivers. For example, some caregivers may prefer a loud, audible notification while others may prefer a visual notification, while still others may prefer a silent notification (e.g. a "vibrate" setting on a mobile device) when being alerted to a head angle condition.

Also, some healthcare facility staff or other persons (such as visitors) may not have the requisite authority to configure or operate the head angle monitoring features of the bed 10. The bed controller 122 may include computer logic to restrict or prevent operation of these features by certain persons, or to enable these features only for certain other persons, based on the biometric data of persons accessing the bed.

The bed 10 may be equipped with pressure sensors, such as transducers, strain gauges, capacitive, optical or piezoelectric sensors, or the like, which detect changes in pressure applied to different sections of the mattress 22 or pressure inside of the bed's mattress (if the bed's mattress has air bladders). The bed controller 122 includes computer-executable instructions that determine, based on the output of a pressure sensor or sensors, the pressures within air bladders or zones of air bladders of the mattress 22. The bed controller 122 may then determine that a bed condition has occurred based on the pressure sensor output, such as a bottoming out condition or a max-inflate condition. The bed controller 122 may alternatively or in addition issue control signals to inflate or deflate certain air bladders based on the output of the pressure sensors, as may be the case when the bed is operating in a pressure relief mode or a therapy mode. The bed controller 122 may issue a visual and/or audible signal, and/or a communication signal relating to the mattress condition or status. Some examples of beds having sensors responsive to mattress conditions are disclosed in U.S. Pat. Nos. 6,505,368; 7,260,860; 7,330,127; 7,469,436; and 7,617,555.

The bed controller 122 may enable a caregiver to turn a particular mattress feature on or off for a particular patient, or to configure a particular mattress feature differently for different patients or differently for different patient conditions. For example, the bed controller 122 may permit a caregiver to set rotation angles, percussion or vibration parameters, cycle times or therapy duration times differently for different patients or patient conditions.

The bed controller 122 may also enable the mattress features to be configured differently for different caregivers. For example, some caregivers may prefer to receive notifications and/or reminders, e.g. those relating to start and end times for mattress features, more or less frequently than other caregivers.

Also, some healthcare facility staff or other persons (such as visitors) may not have the requisite authority to configure or operate one or more of the mattress features of the bed 10. The bed controller 122 may include computer logic to restrict or prevent operation of these features by certain persons, or to enable these features only for certain other persons, based on the biometric data of persons accessing the bed.

Typically, the bed 10 includes a number of siderails, such as opposing siderails 56 and opposing siderails 58, a pair of opposing endboards (e.g. a headboard and a footboard, not shown). A proximity sensor, switch, or other suitable device may be coupled to the siderails and to the bed controller 122 to detect when the siderails are up or down. The bed controller 122 may then issue a visual and/or audible signal and/or communication signal relating to the status of the siderails 56, 58. For example, the bed controller 122 may alert a caregiver if one or more of the siderails 56, 58 are down. An example of a bed having a siderail down sensor is disclosed in U.S. Pat. No. 6,021,533.

The bed controller 122 may enable a caregiver to turn the siderail monitoring features on or off for a particular patient, or to configure the siderail monitoring feature differently for different patients or differently for different patient conditions.

The bed controller 122 may also enable the siderail monitoring features to be configured differently for different members of a healthcare facility staff. For example, some members of a healthcare facility staff may not be permitted to lower the siderails on the beds for particular patients or for any patients.

The sensors with which the bed 10 is equipped may output data signals in discrete or continuous, analog or digital form. The bed 10 is equipped with appropriate signal processing circuitry and/or devices (e.g. analog-to-digital converters, digital-to-analog converters, filters, and the like) to enable the communication of signals between the sensors and the bed controller 122 and the processing of the signals by the bed controller 122.

The electronically-controllable features and functions of the bed 10 may be activated, configured, and deactivated by user inputs that are translated into electrical signals and forwarded to the bed controller 122 by input devices or input-output devices such as foot pedals, buttons, switches, dials, slides, and the like, as well as graphical user interface modules and/or touchscreens.

For example, the bed 10 has a number of foot pedals 80. The foot pedals 80 are coupled to and supported by the base 12. The foot pedals 80 are in electrical communication with the bed controller 122 and may be used by a caregiver to change the position of the bed 10, or to control the casters (e.g. activate or deactivate a brake or steer lock mechanism), or to activate or deactivate some other feature of the bed 10. Stepping on a foot pedal issues a control signal to the bed controller 122, using existing or newly developed techniques. Some examples of beds with foot-operated controls are disclosed in U.S. Pat. Nos. 6,691,346; 6,978,500; and 7,171,708.

The bed 10 also has a caregiver input-output device 60 and a patient input-output device 62, which are configured to permit caregivers and patients, respectively, to activate and deactivate certain electronically-controllable features of the bed 10 using their hands, fingers, or a hand-held instrument.

A caregiver input-output device 60 receives and processes electrical input (e.g. voltage) from one or more controls mounted thereto, which enable a caregiver to configure, activate and/or deactivate certain of the electronically-controllable bed functions. For example, some beds permit the caregiver to raise and lower the bed or change the position of certain sections thereof, change the length or width of the bed, or to achieve a chair, CPR, Trendelenburg, or reverse Trendelenburg position, or to activate certain mattress therapies (such as lateral rotation, percussion, or vibration), by physically contacting the selected control. The illustrated caregiver input-output device 60 includes a biometric input device 104, described below, and at least one non-biometric input device 106, 108. The input device 106 is a button that enables the caregiver to place the bed 10 into a chair position in which the head section 50 is elevated and the foot section 20 is rotated downwardly toward the floor. The input-output device 108 is a graphical touchscreen user interface that has a number of menus and caregiver controls that allow a caregiver to activate, deactivate, or configure features of the bed 10.

The caregiver input-output device 60 includes circuitry configured to convey voltage generated by the controls mounted thereto to the bed controller 122. In the illustrated embodiment, a caregiver input-output device 60 is mounted to the outwardly facing side of at least one of the siderails 58 of the bed 10 (i.e., facing away from the mattress), but the caregiver input-output device 60 may be placed in any suitable location that is accessible to a caregiver. For example, some caregiver controls may be provided on a wall-mounted device or remote control device.

The patient input-output device 62 receives and processes electrical input (e.g. voltage) from number of manually operable controls (such as membrane switches, keys, dials, levers, or the like) coupled to the patient input-output device 62, which enable a patient to activate and deactivate certain bed functions when the patient is positioned on the bed 10. For example, some beds permit the patient to raise and lower the bed or change the position of certain sections thereof by touching these controls. The illustrated patient input-output device 62 includes a biometric input device 102, described below, as well as a number of non-biometric input devices 100.

The patient input-output device 62 includes circuitry to convey voltage generated by the manually operable controls, including the biometric input device 102, to the bed controller 122. In the illustrated embodiment, a patient input-output device 62 is mounted to the inwardly facing side of at least one of the siderails 58 of the bed 10 (i.e., facing toward the mattress), but the patient input-output device 62 may be placed in any suitable location that is accessible to a person using the bed 10. For example, some patient controls may be provided on a pendant controller or remote control device.

The biometric input devices 102, 104 each include one or more biometric sensors, e.g. sensors or scanning devices that are configured to obtain data that identifies a human attribute, which distinguishes one human person from another. In the illustrated embodiment, the biometric input-output devices 102, 104 are fingerprint scanners; however scanners or sensors that obtain data to identify people by their iris, voice pattern, facial pattern, or other distinguishing physical characteristic may also be used. The biometric input-output devices 102, 104 each include a plate or panel that receives a person's fingerprint thereon, and a sensor that scans the person's fingerprint. The fingerprint data is stored in memory at the respective patient or caregiver input-output device 60, 62, or at the bed controller 122.

The input received through the biometric devices 102, 104, may be used to restrict access to certain bed functions to only certain users, or to control access to one or more of the electronically-controllable bed functions, or to configure one or more of the electronically-controllable bed functions differently for different users or different user conditions.

The biometric input-output devices 102, 104 may eliminate the need for patients, caregivers, and other healthcare facility personnel, to carry locating and tracking tags. Also, as the data obtained by the use of the biometric input-output devices 102, 104 is uniquely personal and not removable from the person, it provides greater accuracy and reliability than tags, which can be lost or worn by different persons.

The biometric input-output devices 102, 104 are installed in the caregiver and patient input-output devices 60, 62, respectively. In the illustrated embodiment, the biometric input-output devices 102, 104 are mounted to vertical surfaces of the siderails 58. However, the biometric input-output devices 102, 104 may be mounted to horizontal surfaces of the siderails 58, or may be installed on one or more of the siderails 56, endboard 52 (e.g. a headboard or footboard), or on a pendant controller that is coupled to the bed by a USB or other suitable connector. In general, the location of the biometric input-output devices 102, 104 is not important as long as the biometric input and/or data relating thereto can be accessed and used by the bed controller 122.

As shown, the biometric input-output devices 102, 104 are separate from the other bed controls (e.g. 100, 104, 106, 108) of the caregiver and patient input-output devices 60, 62. This allows biometric input to be obtained independently of input relating to the bed controls. The biometric input may be obtained once, at one of the input devices 102, 104, and then used to determine the level of access to the other bed controls that is appropriate for the user identified by the biometric data. Thus, two actions are required in order to activate (or deactivate or configure) a bed function. A user is required to first touch the biometric input-output device 102, 104, and then touch the appropriate bed function control (e.g. 100, 104, 106, 108).

However, in other embodiments, one or more of the traditionally non-biometric controls (e.g. 100, 104, 106, 108) may have a biometric input-output device integrated therewith. In these embodiments, only one action is required to activate (or deactivate or configure) a bed function. A user touches the integrated biometric and non-biometric control, and the bed controller 122 determines whether the user is authorized to perform the bed function associated with the control. If the user is authorized, the bed controller 122 then automatically proceeds to initiate the requested function without further action required of the user.

The biometric input-output devices 102, 104 may be enabled or disabled, depending on the requirements of a particular implementation of the bed 10. In some implementations, such as the home, perhaps, it may be desirable to temporarily or permanently turn off the biometric features, and this can be done through the touchscreen user interface 108 of the caregiver input-output device 60.

Figure 2:
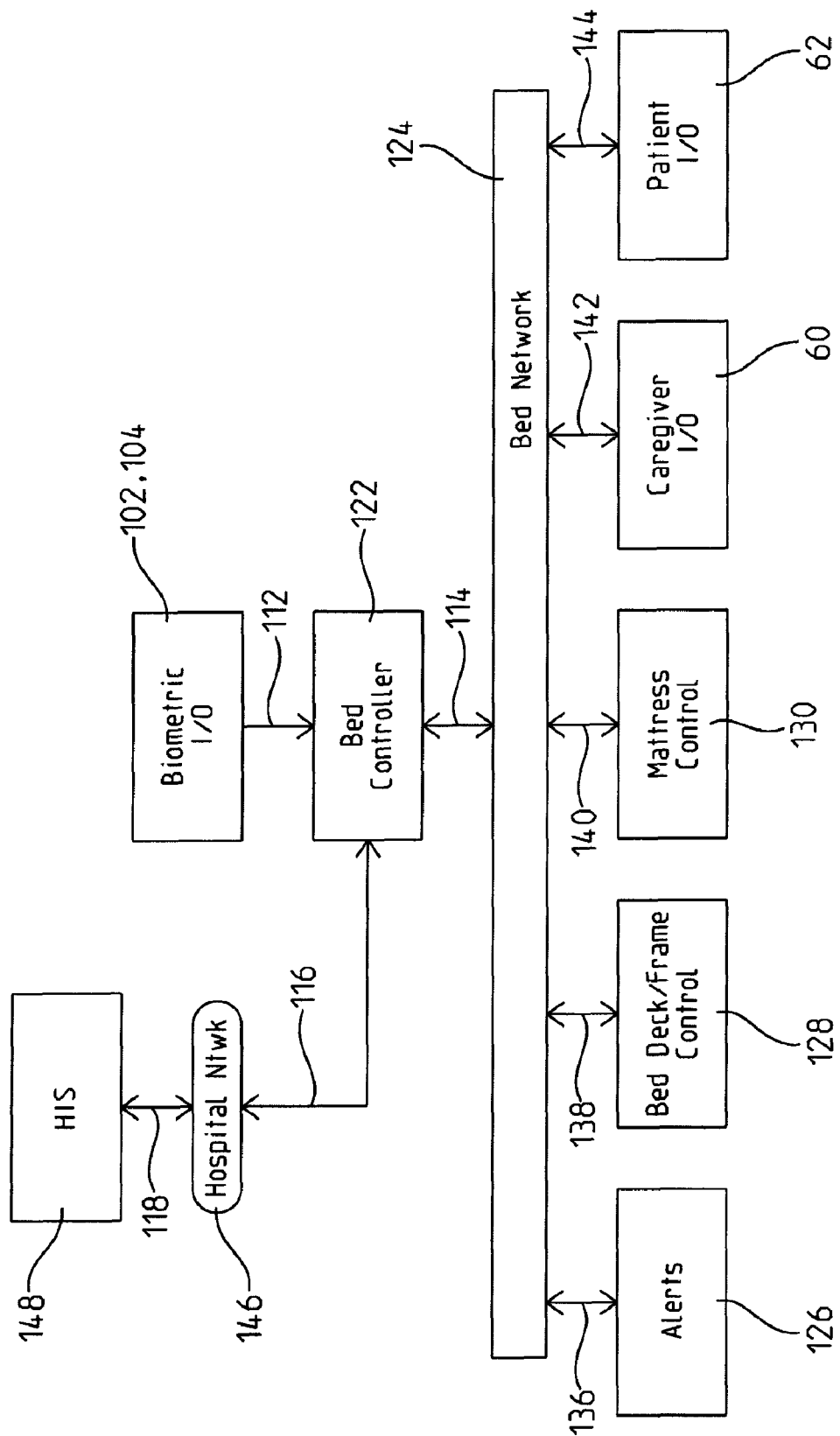
FIG. 2 is a block diagram illustrating a bed control system, including a connection to a communication network.

Referring to FIG. 2, the electronically-controllable functions of the bed 10 are managed by a bed control system that includes the bed controller 122 and a number of bed function control modules, such as the modules 126, 128, 130. The bed controller 122 and each of the bed function control modules 126, 128, 130 include one or more microprocessors or microcontrollers and electrical circuitry mounted on one or more substrates (e.g. printed circuit boards), and typically located in a housing that is mountable to the bed 10.

In the illustrated embodiment, the bed controller 122 is located between the inwardly facing and outwardly facing sides of each of the siderails 58, so that the patient input-output device 62 and the caregiver input-output device 60 are connected to opposite sides of the bed controller 122. The bed function control modules 126, 128, 130 are coupled to the frame 46. However, the bed controller 122 and the bed function control modules 126, 128, 130 may be placed in any suitable location on the bed or elsewhere. The location of the bed controller 122 and the bed function control modules 126, 128, 130 relative to the bed 10 is not important for the purposes of the present disclosure. Also, the bed controller 122 and each of the bed function control modules 126, 128, 130 may comprise a number of different units or sub-modules rather than being contained in a single housing. For example, components of the bed controller 122 and/or any of the bed function control modules 126, 128, 130 may be distributed across multiple storage and/or computing devices connected by a network.

In general, the bed controller 122 receives electrical input from the bed function modules or devices, which include an alerts module 126, one or more deck and frame control modules 128, a mattress control module 130, the biometric input-output devices 102, 104, the caregiver input-output module 60, and the patient input-output module 62, via one or more bidirectional electrical signal paths 136, 138, 140, 142, 144, a bed network 124, and a bidirectional signal path 114.

The bed controller 122, modules 60, 62, 102, 104, 126, 128, 130, and signal paths 112, 114, 136, 138, 140, 142, 144 are arranged according to a suitable system architecture to allow bidirectional electrical communication therebetween. In some embodiments, a peer-to-peer architecture is used, while in others, a Controller Area Network using a serial bus to connect the bed controller 122 and modules 60, 62, 102, 104, 126, 128, 130, is used. In some embodiments, the bed controller 122 and modules 60, 62, 102, 104, 126, 128, 130 are arranged according to a masterless system architecture in which each module is capable of operating substantially autonomously. In other embodiments, a master-slave relationship exists between the bed controller 122 and one or more of the modules 60, 62, 102, 104, 126, 128, 130. The signal paths 112, 114, 136, 138, 140, 142, 144 may include wired (e.g. twisted conductor pair) or wireless connections. Examples of these bed control system architectures are described in U.S. Pat. Nos. 5,771,511; 6,584,628; 7,237,287; 7,296,312; 7,451,506; 7,480,951; and 7,657,956.

In general, each of the modules 60, 62, 102, 104, 126, 128, 130 is connected to its appropriate sensors and actuators so that it can perform its assigned function or functions. The alerts module 126 detects the angles and/or positions of the frame 46 and all the appropriate bed deck sections. It interfaces with bed-not-down sensors, patient position monitoring sensors, and/or siderail position sensors. The alerts module 126 executes computer logic to determine, based on set parameters relating to acceptable bed positions or angles as determined according to the requirements of a particular design, implementation, or use of the bed 10, whether to generate an alert (e.g. an electronic, audio or visual indication relating to the status of the bed). The determination of whether to generate an alert may be based on patient or caregiver information that is available to the alerts module 126 as a result of inputs received by the biometric input-output devices 102, 104, as described below. The alerts module 126 outputs bed status and/or alert information to the bed network 124 for use by the bed controller 122 and/or other modules or devices.

The bed deck/frame control module 128 controls the articulation and movement of the frame 46 and the movable sections of the deck 18. The bed deck/frame control module 128 accepts inputs from various user interfaces and controls (e.g. the caregiver and patient input-output devices 60, 62), to control bed movement, adjustment, and articulations, to, for example, change the position or orientation of the deck or frame, adjust the length of the bed, and/or adjust the width of the bed. The bed deck/frame control module 128 executes computer logic to determine, based on inputs from sensors coupled to the bed's actuators, the actual position of the bed deck sections. The bed deck/frame control module 128 determines whether the position of any of the deck sections should be adjusted, based on various inputs, and issues control signals to the bed actuators to initiate movement, adjustment, or articulation as needed. The determination of whether or to what degree or extent to articulate or move the bed or parts thereof may be based on patient or caregiver information that is available to the bed deck/frame control module 128 as a result of inputs received by the biometric input-output devices 102, 104, as described below.

In embodiments that include an on-board weigh scale, the bed deck/frame control module 128 also controls the operation of the weigh scale. The bed deck/frame control module 128 receives signals from the weigh sensors (e.g. load beams) and executes computer logic to translate the signals into an actual weight value. The bed deck/frame control module 128 outputs the weight value to the bed network 124 for display purposes, for communication to the hospital network 146, or for use by other modules or devices. The determination of whether to use the on-board weigh system to weigh a particular person, or how to calculate the weight of a particular person, may be based on patient or caregiver information that is available to the bed deck/frame control module 128 as a result of inputs received by the biometric input-output devices 102, 104, as described below.

The mattress control module 130 controls the operation of the mattress 22, if the mattress 22 includes air features (e.g. low air loss) and/or air bladders, where the supply of air thereto is automated or automatically adjusted based on changes in parameters. The mattress control module 130 accepts input from the caregiver input-output module 60 relating to desired bladder pressure and/or mattress therapies (e.g. percussion, vibration, rotation). The mattress control module 130 executes computer logic to process inputs received from the caregiver input-output module 60 and/or other modules (e.g. the bed weighing system) and send control signals to the mattress's air control unit (not shown) to control or adjust the supply of air to different parts of the mattress as needed. The determination of whether to initiate a particular mattress therapy, adjust the pressure in one or more sections of the mattress 22, or supply or remove air from a portion of the mattress, may be based on patient or caregiver information that is available to the mattress control module 130 as a result of inputs received by the biometric input-output devices 102, 104, as described below.

The bed controller 122 may receive input directly from the biometric input-output devices 102, 104 via an electrical signal path 112. The biometric input-output devices 102, 104 may be connected to the bed controller 122 through the bed network 124 and signal path 114. Also, the biometric input-output devices 102, 104 may be connected to the bed controller 122 through the caregiver input-output device 60 and/or the patient input-output device 62 as noted above.

The bed controller 122 may be connected to the communication network 146, which connects the bed 10 to a hospital or other facility in or in connection with which the bed 10 is used, via a bidirectional signal path 116, in order to send and/or receive data and/or instructions to/from a healthcare information system 148. The healthcare information system 148 may include one or more networked systems, such as an admission, discharge, and transfer (ADT) system, an electronic medical records (EMR) system, and a nurse call system. An example of a system in which a bed network communicates with an ADT system is disclosed in U.S. patent application Ser. Nos. 12/708,891, filed Feb. 19, 2010, and 12/711,912, filed Feb. 24, 2010. It will be understood that some of these processes and systems, or portions of them, may not be performed by or physically located at the facility in which the bed is used. For example, data storage and/or processing, or portions thereof, may be performed by other entities or at other locations.

The signal paths 116, 118 may include wired or wireless connections, or may be connected to an electronic network, such as an Ethernet network, which may be configured according to a TCP/IP or other suitable electronic communications protocol. In general, each of the representative signal paths 112, 114, 116, 118, 136, 138, 140, 142, 144 may include one or more signal paths therein as may be needed to accomplish the sending and receiving of data and/or instructions between or among the various modules and systems.

Among other things, the bed controller 122 processes inputs from the modules 60, 62, 102, 104, 126, 128, 130, stores data in and retrieves data from memory, and executes computer logic to control the operation of the various electronically-controllable features of the bed 10. The logic, functions and processes identified herein as being part of the modules 60, 62, 102, 104, 126, 128, 130 may be included in the bed controller 122 or may be implemented as one or more separate modules that are in communication with the bed controller 122. Additionally, the bed controller 122 itself may be implemented as a single module or a number of distributed modules.

Figure 3:
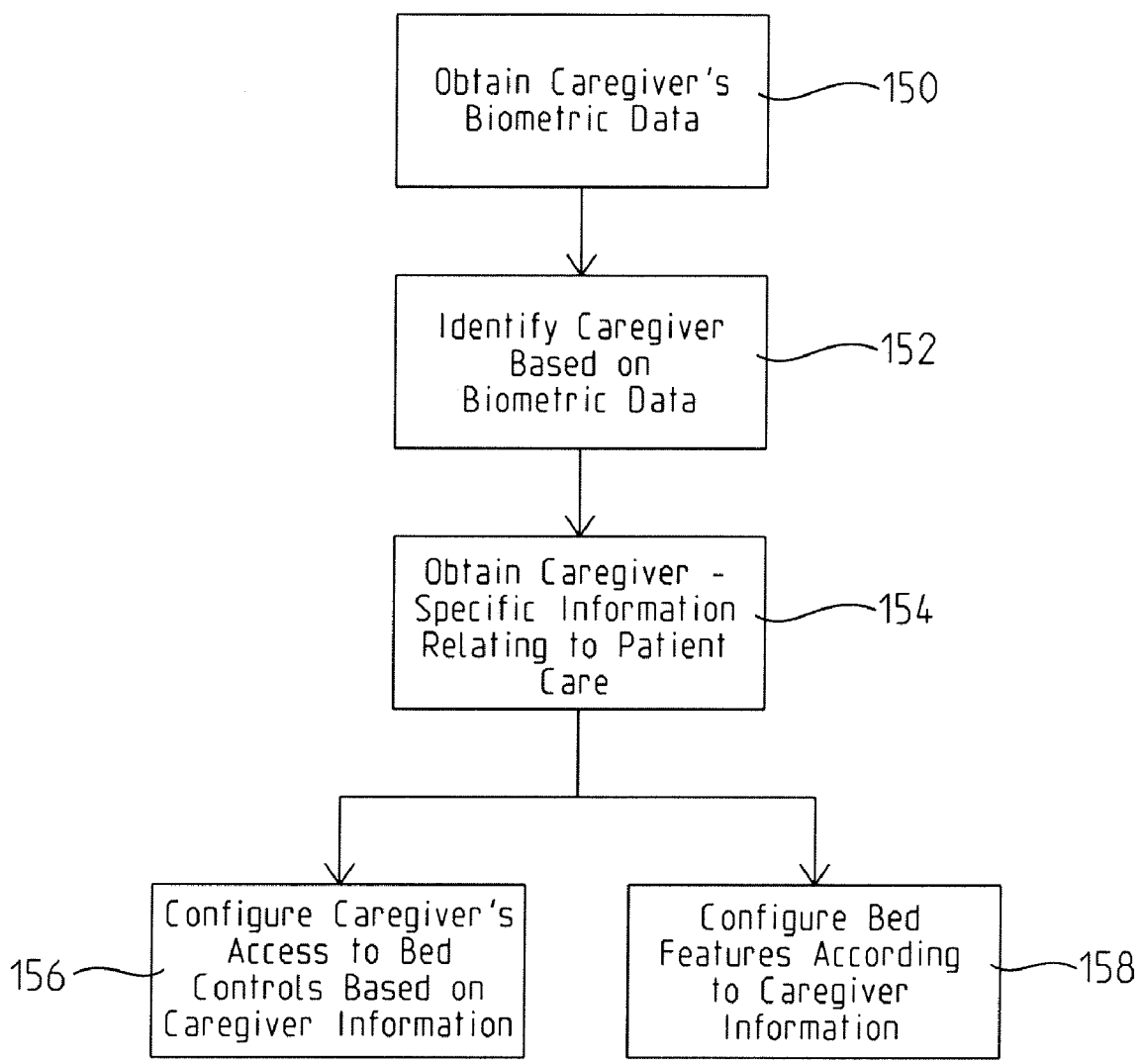
FIG. 3 is a flow diagram illustrating a biometric bed configuration process executable by the bed control system.

FIG. 3 illustrates steps or routines of a process that may be implemented using computer circuitry and/or programming, stored in memory, and executed by the bed controller 122 and/or the modules 60, 62, 102, 104, 126, 128, 130 to control electronically-controllable features of the bed 10 based on biometric data of a caregiver.

In routine 150, a caregiver's biometric data is obtained. In the illustrated embodiment, the biometric data is obtained by the caregiver touching the biometric input-output device 104 with the pad of a finger. The caregiver's biometric data (e.g. fingerprint pattern) is received by the biometric input-output device 104 and stored in memory, at the biometric input-output device 104 and/or the bed controller 122. While the term "caregiver" is used herein for convenience, the described processes also apply to persons other than those traditionally known as caregivers (such as visitors, service technicians, housekeeping staff, administrators, and the like).

Once stored in memory, the biometric data may be used to generate reports detailing the history of activity occurring at the bed 10 over time. In embodiments where individual bed function controls each have their own biometric sensor integrated therewith, the biometric data may be used to accumulate an extremely detailed accounting of specific bed functions activated, deactivated, and configured by or for individual caregivers.

The caregiver activity history associated with the biometric data may also be used by the bed controller 122 to generate alerts or reminders. For instance, the bed controller 122 may keep track of the last time the caregiver touched the biometric input-output device 104, and send the caregiver an electronic reminder to return to the bed 10 at a specific time, according to a particular protocol that has been previously set for the caregiver and the patient using the bed 10.

In routine 152, the caregiver's biometric data is mapped to caregiver information that has previously been stored in a database, table, listing, file, or other suitable data structure, at the biometric input-output device 104, the bed controller 122, and/or the HIS 148. For example, in one implementation, caregiver biometric data is obtained from each caregiver upon hiring by the facility, and stored in the HIS 148. This data is accessible to bed control systems of various beds of the facility, including the bed 10, via the hospital network 146. Using existing or newly developed fingerprint mapping algorithms, the biometric data received at the biometric input-output device is compared with the stored biometric data, and the particular caregiver associated with the biometric data received at the biometric input-output device 104 is uniquely identified.

The routine 154 uses the biometric data obtained at the biometric input-output device 104 to access data about the caregiver, the caregiver's duties, activities, and/or status, as may be needed by the bed controller 122 or a particular module 60, 62, 112, 114, 126, 128, 130 of the bed control system. This data includes, for example, indications of the caregiver's rank within the facility (e.g. technician, service personnel, nurse, RN, LPN, clinician, therapist, physician, visitor, family member, etc), as well as indications as to whether the caregiver is on or off active duty, or whether the caregiver is assigned to the particular patient using the bed at which the biometric data was obtained.

The routine 156 analyzes the caregiver information obtained through the use of the biometric data, determines whether the caregiver's access to the electronically-controllable features of the bed 10 should be modified, reconfigured, or limited in any way, and causes the appropriate result to occur at the bed 10. For instance, if the routine 154 determines that the caregiver is not assigned or related to the patient using the bed at which the caregiver's biometric data was obtained (according to the HIS, for example), the routine 156 may disable all of the controls at the caregiver input-output device 60. If the caregiver is permitted to articulate the patient's bed but not initiate any of the mattress controls, then the routine 156 may enable the bed articulation controls (e.g. control 106) but disable the mattress therapy controls (e.g. the user interface 108). If the person is a service technician, the routine 156 may enable access to a portion of the user interface 108 that is specifically configured for use by service technicians, and disable the other electronically-controllable features of the bed.

If the routine 156 determines that one or more of the bed functions should be enabled for the caregiver identified by the biometric data, then the routine 156 may wait a period of time for the caregiver to activate one of the permitted bed controls. If no action is taken by the caregiver within the period of time, then the bed 10 will require the biometric data to be input again. A message or other indication that the period has "timed out," or a prompt to touch the biometric sensor again, may be displayed on the user interface 108 or output aurally at the caregiver input-output device 60.

In embodiments where individual bed function controls each have a biometric sensor integrated therewith, the biometric data is used to enable or disable the particular bed function associated with the touched control. For instance, in one embodiment, when a caregiver touches the bed control 106, the caregiver's biometric data is obtained by the biometric sensor integrated with the bed control 106. The bed controller 122 and/or caregiver input-output device 104 determines whether the caregiver is entitled to activate the bed function controlled by the bed control 106. If the caregiver is not entitled to activate the bed control 106, then the bed function will not be activated, but other bed controls will not be affected. If the caregiver is entitled to activate the bed control 106 (based on the biometric data), the bed controller 122 may wait a period of time for the caregiver to press the bed control 106 a second time, before initiating the bed function, or may proceed to initiate the bed function without requiring further action by the caregiver.

The routine 158 configures one or more of the electronically-controllable bed features based on the caregiver information associated with the biometric data obtained by the biometric input-output device 104. For example, in some implementations only certain caregivers may be permitted to set the head angle of the bed below thirty degrees, or configure mattress therapy parameters (such as percussion and vibration duration and/or rates, turning angles, rotation cycles, etc.) in a certain way. The user interface 108 typically includes touchscreen displays that allow caregivers to activate, deactivate or configure these and other features of the bed 10. The routine 158 may limit the available choices for configuring therapy rates, angles, or durations, in response to the biometric input.

FIG. 4 illustrates steps or routines of a process that may be implemented using computer circuitry and/or programming, stored in memory, and executed by the bed controller 122 and/or the modules 60, 62, 102, 104, 126, 128, 130 to control electronically-controllable features of the bed 10 based on biometric data of a patient.

In routine 160, the biometric data of a person using the bed 10 (referred to herein as a "patient" for convenience, although persons other than patients may also use the bed) is obtained. In the illustrated embodiment, the biometric data is obtained by the patient touching the biometric input-output device 102 with the pad of a finger. The patient's biometric data (e.g. fingerprint pattern) is received by the biometric input-output device 102 and stored in memory, at the biometric input-output device 102 and/or the bed controller 122.

Once stored in memory, the patient's biometric data may be used to generate reports detailing the history of activity occurring at the bed 10 and relating to the identified patient over time. In embodiments where individual bed function controls each have their own biometric sensor integrated therewith, the biometric data may be used to accumulate an extremely detailed accounting of specific bed functions activated and/or deactivated by the patient.

In routine 162, the patient's biometric data is mapped to patient information that has previously been stored in a database, table, listing, file, or other suitable data structure, at the biometric input-output device 102, the bed controller 122, and/or the HIS 148. For example, in one implementation, the patient's biometric data is obtained from each patient upon admission to the facility (e.g. via an ADT system), and stored in the HIS 148. This data is accessible to bed control systems of various beds of the facility, including the bed 10, via the hospital network 146. Using existing or newly developed fingerprint mapping algorithms, the biometric data received at the biometric input-output device is compared with the stored biometric data, and the particular patient associated with the biometric data received at the biometric input-output device 102 is uniquely identified.

The routine 164 uses the biometric data obtained at the biometric input-output device 102 to access data about the patient, including portions of the patient's medical history or electronic medical record (EMR), as may be needed by the bed controller 122 or a particular module 60, 62, 102, 104, 126, 128, 130 of the bed control system. This data includes, for example, indications of the patient's vital statistics (e.g. height, weight, age, etc.), status at the facility (e.g. returning from surgery, returning from therapy, etc.), health condition (e.g. fall risk, pressure ulcer risk, etc.), and caregivers or other staff assigned to the patient.

The routine 166 analyzes the patient information obtained through the use of the biometric data, determines whether the patient's access to the electronically-controllable features of the bed 10 should be modified, reconfigured, or limited in any way, and causes the appropriate result to occur at the bed 10. For instance, if the routine 164 determines that the patient is at risk for falling, the routine 166 may disable one or more of the bed articulation controls 100 at the patient input-output device 62 (e.g. a "chair" position control that places the bed in the chair position), or may activate the siderail down alarm. If the routine 164 determines that the patient has just returned from surgery, the routine 166 may disable the "head down" bed articulation control, so that the patient cannot lower the head section of the bed below 30 degrees. If the routine 164 obtains the patient's weight information (from the HIS 148, for example), based on the biometric data, then the routine 166 may disable the bed's weigh scale.

If the routine 166 determines that one or more of the bed functions available to the patient should be enabled for the patient identified by the biometric data, then the routine 166 may wait a period of time for the patient to activate one of the permitted bed controls. If no action is taken by the patient within the period of time, then the bed 10 will require the biometric data to be input again.

In embodiments where individual bed function controls each have a biometric sensor integrated therewith, the patient's biometric data may be used to enable or disable the particular bed function associated with the touched control. For instance, in one embodiment, when a patient touches a head down control or chair position control (e.g. 100), the patient's biometric data is obtained by the biometric sensor integrated with the touched control 100. The bed controller 122 and/or patient input-output device 102 determines whether the patient is entitled to activate the bed function controlled by the touched control 100. If the patient is not permitted to activate the control, then the bed function will not be activated, but other bed controls will not be affected. If the patient is entitled to activate the control (based on the biometric data), the bed controller 122 may wait a period of time for the patient to press the bed control 100 a second time, before initiating the bed function, or may proceed to initiate the bed function without requiring further action by the patient.

The routine 168 configures a caregiver's access to one or more of the electronically-controllable bed features based on the patient information associated with the biometric data obtained by the biometric input-output device 102. For example, if the patient has just returned from surgery, the caregiver assigned to the patient may wish to restrict access to certain bed functions by other caregivers, who may be unaware of the patient's status, for a certain amount of time. The routine 168 may allow the assigned caregiver, determined based on the caregiver's biometric data obtained at the biometric input-output device 104, to disable the head down bed control for the patient and/or for other caregivers, using the touchscreen user interface 108. As another example, if the patient information associated with the patient's biometric data indicates that the patient is at risk for falling upon exiting the bed, the bed controller 122 may "lock" the bed exit alarm feature of the bed so that the bed exit alarm cannot be turned off by a caregiver.

The routine 170 configures one or more electronically-controllable bed features according to patient information associated with the patient identified by the biometric data obtained by the biometric input-output device 102. For example, the patient's height, weight or medical history information may be obtained from the HIS 148 or otherwise made available to the bed controller 122 as a result of the biometric data. In this instance, the bed controller 122 executes computer logic to determine the appropriate actuator/bed articulation parameters (such as speed and/or duration of actuator function) and/or mattress inflation pressures based on the patient's height, weight, and/or medical history information. When a particular bed articulation request is made (by either a caregiver or the patient), the bed controller 122 executes the articulation request using the articulation parameters as customized or modified for the patient's height and weight. For example, the foot section of the bed may be extended a greater amount if the patient is taller than a preset patient height, the seat section of the mattress may be inflated to a higher pressure if the patient is heavier than a certain weight, and/or actuators may be adjusted to articulate deck sections more slowly if the patient has just returned from surgery.

Also, the bed controller 122 may automatically adjust the bed configuration upon learning certain patient information as a result of the biometric features described above. For example, the width of the bed or certain deck sections thereof may be adjusted based on the patient's height and/or weight. These adjustments may be initiated by the bed controller 122 automatically upon obtaining height, weight, or other patient-specific information linked to the biometric data as described above, without requiring further input from a user, or may be initiated by a caregiver, e.g. by pressing a 'configure bed' button located on a caregiver input/output device 60.

There are many advantages of the present disclosure arising from the various features described herein. It will be noted that alternative embodiments of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A bed system, comprising
 a bed having at least one electronically-controllable feature,
 a biometric sensor operably coupled to the bed, the biometric sensor being configured to receive a first input from a user,
 a non-biometric input device operably coupled to the bed, the non-biometric input device being configured to receive a second input from the user to activate an electronically-controllable feature of the bed, and
 a controller operably coupled to the bed, the biometric sensor, and the non-biometric input device, the controller being configured to analyze the first input and output a control signal to enable or disable the non-biometric input device based on the first input.

2. The bed system of claim 1, wherein the controller uniquely identifies the user based on the first input.

3. The bed system of claim 1, wherein the controller identifies a characteristic of the user based on the first input.

4. The bed system of claim 3, wherein the controller determines whether access to an electronically-controllable feature of the bed should be enabled or disabled based on the characteristic of the user.

5. The bed system of claim 1, wherein the controller determines whether the user is a patient or a caregiver based on the first input.

6. The bed system of claim 1, comprising a communication link operably coupled to the controller to provide data representative of the first input to a healthcare information system and to provide data relating to the user from the healthcare information system to the controller.

7. The bed system of claim 6, wherein the controller determines whether access to an electronically-controllable feature of the bed should be modified based on the data from the healthcare information system.

8. A bed system, comprising
 a bed having at least one electronically-controllable feature,
 a biometric sensor operably coupled to the bed, the biometric sensor being configured to receive a first input from a user,
 a non-biometric input device operably coupled to the bed, the non-biometric input device being configured to receive a second input from the user and being operable to activate or deactivate an electronically-controllable feature of the bed in response to the second input, and
 a controller operably coupled to the bed, the biometric sensor, and the non-biometric input device, the controller being configured to analyze the first input and determine based on the first input whether to activate the electronically-controllable feature of the bed in response to the second input.

9. The bed system of claim 8, wherein the biometric sensor is integrated with the input device.

10. The bed system of claim 8, wherein the biometric sensor is spaced from the input device.

11. The bed system of claim 8, comprising at least one of a siderail and an endboard coupled to the bed, wherein the biometric sensor is mounted to one of the siderail and the endboard.

12. The bed system of claim 8, comprising a pendant controller coupled to the bed, wherein the biometric sensor is mounted to the pendant controller.

13. The bed system of claim 8, comprising a second biometric sensor, wherein the biometric sensor is mounted to the bed at a first location, the second biometric sensor is mounted to the bed at a second location spaced from the first location, the second biometric sensor is configured to receive a third input from a user, and the controller analyzes the third input to determine whether to activate an electronically-controllable feature of the bed based on the third input.

14. A bed system, comprising
 a bed having at least one electronically-controllable feature, a biometric sensor operably coupled to the bed, the biometric sensor being configured to receive a first input from a user, a non-biometric input device operably coupled to the bed, the non-biometric input device being configured to receive a second input from the user, and a controller operably coupled to the bed, the biometric sensor, and the non-biometric input device, the controller being configured to analyze the first input, modify an electronically-controllable feature of the bed in response to the first input, and initiate operation of the modified electronically-controllable feature in response to the second input.

15. The bed system of claim 14, wherein the controller determines whether the user is a patient or a caregiver based on the first input and configures the electronically-controllable feature based on whether the user is a patient or a caregiver.

16. The bed system of claim 14, wherein the non-biometric input device comprises a graphical user interface, the controller determines whether the user is a patient, a caregiver, a visitor, or another person based on the first input, and the controller configures the graphical user interface based on whether the user is a patient, a caregiver, a visitor, or another person.

17. The bed system of claim 14, wherein the controller determines a characteristic of the user based on the first input and configures the electronically-controllable feature based on the characteristic of the user.

18. The bed system of claim 14, wherein the electronically-controllable feature is a bed articulation feature, the characteristic of the user indicates that the user has a health condition, and the controller adjusts the bed articulation feature based on the health condition.

19. The bed system of claim 14, wherein the electronically-controllable feature is a support surface feature, and the controller adjusts the support surface feature based on the characteristic of the user.

20. The bed system of claim 14, wherein the controller automatically adjusts at least one of a time parameter, a speed parameter, an articulation parameter, a length adjustment parameter, a width adjustment parameter, and an alarm parameter relating to the electronically-controllable feature based on the characteristic of the user.

* * * * *